(12) United States Patent
Flesch

(10) Patent No.: US 6,425,870 B1
(45) Date of Patent: Jul. 30, 2002

(54) METHOD AND APPARATUS FOR A MOTORIZED MULTI-PLANE TRANSDUCER TIP

(75) Inventor: Aimé Flesch, Andrésy (FR)

(73) Assignee: Vermon, Tours Cedex (FR)

( * ) Notice: Subject to any disclaimer, the term of this patent is extended or adjusted under 35 U.S.C. 154(b) by 12 days.

(21) Appl. No.: 09/613,731

(22) Filed: Jul. 11, 2000

(51) Int. Cl.$^7$ ................................................. A61B 8/14
(52) U.S. Cl. ....................................... 600/459; 600/447
(58) Field of Search ................................ 600/444, 445, 600/463, 459, 141, 449, 450, 73, 74, 462, 472, 441, 446, 447

(56) References Cited

U.S. PATENT DOCUMENTS

| | | | | |
|---|---|---|---|---|
| 4,374,525 A | * | 2/1983 | Baba | 600/463 |
| 5,176,142 A | * | 1/1993 | Mason | 600/463 |
| 5,181,514 A | * | 1/1993 | Solomon et al. | 600/444 |
| 5,445,154 A | * | 8/1995 | Larson et al. | 600/459 |
| 5,456,256 A | * | 10/1995 | Schneider et al. | 600/445 |
| 5,704,898 A | * | 1/1998 | Kokish | 600/141 |

FOREIGN PATENT DOCUMENTS

EP 0780088 A1 * 6/1997 ............ A61B/8/08

* cited by examiner

Primary Examiner—Marvin M. Lateef
Assistant Examiner—Ruby Jain
(74) Attorney, Agent, or Firm—Larson & Taylor, PLC

(57) ABSTRACT

An ultrasonic phased array imaging transducer device is provided which includes a flexible sealing membrane disposed within a housing so as to divide the housing into a wet chamber and a dry chamber. The wet chamber contains a fluid and includes a phased array transducer disposed in the tip end of the housing and oriented so as to provide a sound path extending perpendicular to the longitudinal axis of the housing. A motor provides rotation of the transducer while an encoder determines positional information with respect to the transducer. A flexible cable of electrical circuit connections is electrically connected to the transducer and is coiled relative to the transducer so as to permit transducer rotation of more than 180 degrees. The flexible cable extends from the wet chamber through the flexible sealing membrane to the dry chamber. A torque limitation device limits the torque transmitted to the transducer.

14 Claims, 4 Drawing Sheets

METHOD AND APPARATUS FOR A MOTORIZED MULTI-PLANE TRANSDUCER TIP

BACKGROUND OF THE INVENTION

1. Field of the Invention

The present invention relates to ultrasonic probes, and, more particularly, to trans-esophageal imaging ultrasonic probes.

2. Background of the Invention

Commercial trans-esophageal ultrasonic probes are typically provided with either a bi-plane or multi-plane phased-array transducer mounted at the distal tip. The bi-plane device is based on the integration of two phased-array transducers arranged perpendicular to each other, while the multi-plane device uses a transducer which rotates about an axis parallel to the scanning plane. The flexibility and ease of use thereof makes multi-plane transducers the preferred instrument for use in trans-esophageal examinations in spite of the relatively high cost of these transducers.

The fabrication of phased array multi-plane devices is complicated because of the additional mechanical components required to provide rotation of the transducer array. In order to keep the distal end of the device small for ease of insertion into the esophagus (which is typically 12 to 14 mm across), the rotary drive means for the transducer is typically located, remotely, in the handle of the device. The rotary drive means can be a motor or a manual control handle connected to an associated drive shaft as disclosed, for example, in U.S. Pat. No. 4,543,960. A rotating drive shaft typically transfers the rotary motion from the rotary drive means to the distal tip of the device. This handle also controls the articulation of the distal tip in several planes so as to provide remotely controlled transducer positioning. However, with the rotary drive means located in the housing of the handle, errors can be introduced because of "wind-up" in the drive shaft as well as because of a lack of precision associated with the gearboxes or gearing assemblies forming part of the rotary drive means. These sources of error greatly reduce the positional accuracy of the rotating transducer.

Rotating trans-esophageal ultrasound transducers have been developed which incorporate a motor disposed directly in the tip so as to eliminate the inaccuracies discussed above associated with a remotely positioned motor. However, in these transducers, the motor is generally housed in a separate portion of the distal tip from the transducer. Typically, the motor would be housed in a dry chamber and the transducer would be housed in a wet chamber. The wet chamber is filled with an acoustic fluid necessary to provide optimum performance of the transducer. Therefore, rotational seals are required in order to keep the acoustic fluid out of the dry chamber which houses the motor. These seals exert a significant amount of torque on the rotating components that extend through the seals. Because of this increased torque, motors with high torque capabilities are generally required. Integrating such a motor in a miniaturized tip often poses significant problems because high torque motors are generally larger in size than low torque motors.

Rotating trans-esophageal ultrasonic probes are also used for generating three dimensional images. In order to generate a three-dimensional image, multiple images of a two dimensional scan plane must be obtained. Once the two dimensional images are obtained, the images are processed to produce a three dimensional image. For the purposes of trans-esophageal imaging, a longitudinal axis imaging transducer, i.e., a transducer which rotates about the longitudinal axis thereof, is not ideal. Such a transducer is described by U.S. Pat. No. 5,085,221. To use the apparatus in this patent, the physician must first determine the specific region of interest, using standard two dimensional imaging, prior to capturing cardiac images for subsequent three dimensional rendering, and then position the transducer accurately for the three dimensional image capturing. A transverse imaging plane is essential in obtaining this two dimensional information since such an approach can produce a short-axis view of the heart that contains the morphology required for diagnosis. Thus, while a longitudinal image plane device can be utilized to rotate, capture and create a three dimensional rendering, it is difficult to position the device within the esophagus.

SUMMARY OF THE INVENTION

In accordance with the invention, an ultrasonic phased array imaging transducer device is provided which overcomes or significantly reduces important problems associated with prior art devices of the same type, including those discussed above.

According to the invention, an ultrasonic phased array imaging transducer device is provided which comprises: a housing having a longitudinal axis, a tip end and a base end; a flexible sealing membrane disposed within said housing and dividing said housing into a wet chamber and a dry chamber; said wet chamber of said housing containing a fluid and including: a phased array transducer disposed in the tip end of said housing, and oriented so as to provide a sound path extending perpendicular to the longitudinal axis of the housing; a motor for rotating the transducer; an encoder for determining positional information with respect to the transducer; a flexible cable electrically connected to said transducer and coiled relative to said transducer so as to permit transducer rotation of more than 180 degrees; and a torque limitation device for limiting torque transmitted to the transducer; said flexible cable extending from the wet chamber through the flexible sealing membrane to the dry chamber.

Preferably, the membrane comprises an elastic member which expands so as to compensate for expansion of the fluid in the wet chamber.

In a preferred implementation, motor includes a drive shaft and the torque limitation device comprises a first gear fixed to the drive shaft of the motor, a second gear directly mounted on the transducer, and a third gear linking the first gear and the second gear so as to provide transmission of rotary drive from the first gear to the second gear. The third gear is preferably arranged so as to provide disengagement of the transmission responsive to torque in excess of a predetermined value being exerted on said transducer. Advantageously, the torque limitation device includes a fourth gear engaging said second gear and mounted on a support shaft, a further gear affixed to the support shaft and a spring for biassing said third gear into engagement with said further gear so that, when said third gear and said further gear are engaged, said third gear provides said transmission and, when said third gear and said further gear are disengaged, said transmission is interrupted.

Preferably, the transducer includes a peripheral gear and the encoder includes an encoder gear engaged with the peripheral gear of said transducer and a mechanical abutment arrangement for providing mechanical limiting of the rotation of the transducer. Advantageously, the encoder includes an encoder disk, and the peripheral gear and the encoder gear have a relative gear reduction ratio permitting rotation of the transducer more than 360° with a single said encoder disk.

The motor preferably comprises a means for desynchronizing the motor if a predetermined torque output is exceeded.

Advantageously, the tip and base of said housing have an anatomical shape adapted to fit onto a fingertip of a user. The housing is preferably adapted to be mounted to an endocavity ultrasound probe.

In a preferred implementation, the housing is adapted to be mounted at the distal portion of a laparoscopic probe.

Further features and advantages of the present invention will be set forth in, or apparent from, the detailed description of preferred embodiments thereof which follows.

BRIEF DESCRIPTION OF THE DRAWINGS

FIG. 1A is a bottom plan view of the transducer and flexible circuits of the device of FIG. 1;

DESCRIPTION OF THE PREFERRED EMBODIMENTS

Figure 1:
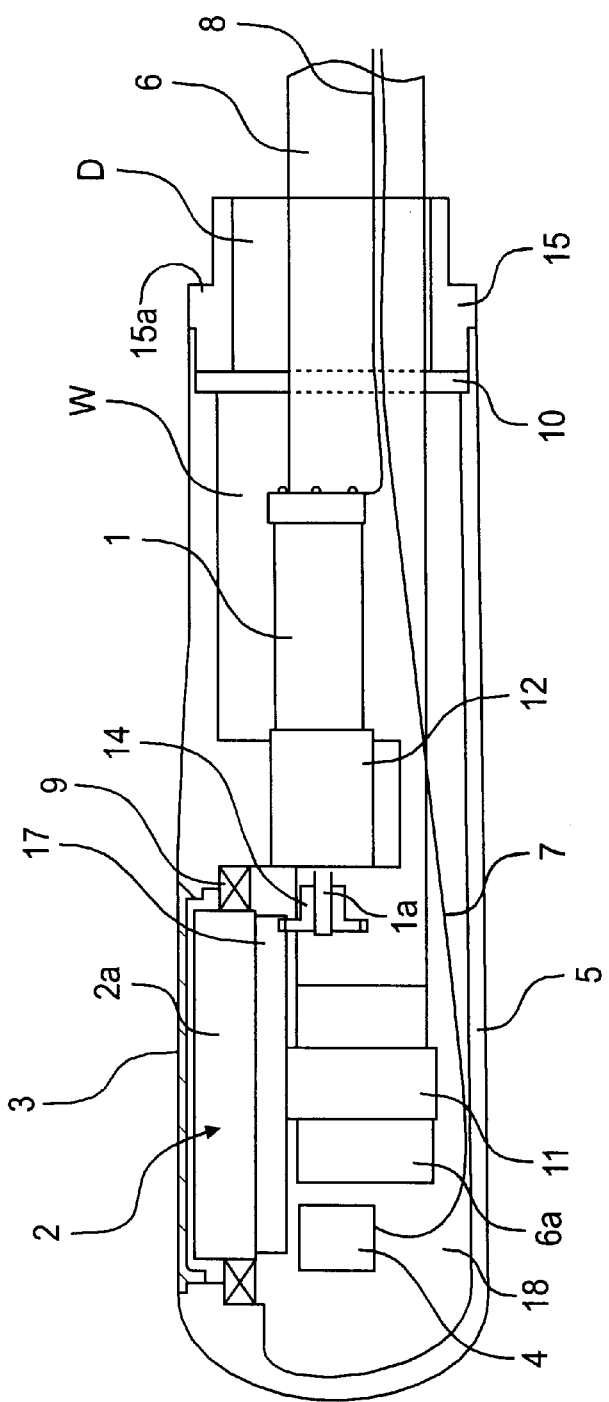
FIG. 1 is a longitudinal cross section view of a transducer device in accordance with a first preferred embodiment of the invention.

Referring to FIG. 1, there is shown a transducer tip constructed in accordance with a first preferred embodiment of the invention. It will be understood that while the invention is described relative to a trans-esophageal ultrasonic endoscope, the invention is not limited to this application. The transducer tip includes a generally cylindrical housing 5 having an acoustic window 3 mounted in a wall thereof near the distal end. The housing 5 includes a transverse flexible membrane 10 which divides the transducer tip into a wet chamber W and a dry chamber D. The wet chamber W is filled with an acoustic coupling fluid and is sealed in order to prevent air or bubbles from entering the wet chamber W. A sheath of flexible circuits 6 (i.e., a plurality of electrical circuits carried by a flexible substrate as described below), an encoder circuit connector wire or conductor 7, and a further connector wire or conductor 8, extend through the air-tight flexible membrane 10 to carry data and control signals to, and from, components or equipment in the wet chamber W (also described in more detail below) so as to control the equipment in the wet chamber W, and communicate data back for display to the user of the device.

A transducer 2, is positioned in registration with the acoustic window 3 which covers the front face of the transducer 2, and which is secured to the housing 5 by, for example, a suitable bonding in or by ultrasonic welding. The transducer 2 is a conventional multi-element array and the array elements of transducer 2 are contained within a circular support member 2a. The support member 2a of transducer 2 rotates within and is maintained in place by a ball bearing 9 and the array elements are supported by an internal support structure (not shown). At the rear of the internal support structure (not shown), a cylindrical take-off shaft 11 is provided which extends rearwardly of transducer 2. The cylindrical shaft 11 provides connection points for the flexible circuits 6 and, to this end, a terminal portion 6a of flexible circuits 6 is wrapped around the cylindrical shaft 11 so as to provide electrical connections between the array elements and the circuits of the sheath of circuits 6 as is described below in connection with FIG. 1A.

The flexible circuits 6 provide the necessary electrical contact or connection between the individual transducer elements of transducer 2 and the individual coaxial cables (not shown) which are, in turn, connected to the remote ultrasound system (not shown). The flexible circuits 6 typically comprise, for example, extended traces of copper on a polymide filler substrate. As shown in FIG. 1A, the flexible circuits 6 permit rotation of transducer 2 by coiling around (and uncoiling from) the central cylindrical shaft 11.

A driven gear 17 is mounted on the underside of the internal support (not shown) and extends around the circumference thereof. The driven gear 17 is mated to, i.e., meshes with, a drive gear or pinion gear 14 which is, in turn, connected to, and is driven by, a motor 1. Drive gear 14 is mounted on an output shaft 1a of motor 1 so as to rotate with shaft 1a. The motor 1 is mounted within a housing along the longitudinal axis thereof and is typically between 3–5 mm in diameter. Motor 1 is preferably equipped with a reduction gearbox 12 provided between drive shaft 1a and motor 1.

A positioning encoder 4 is also mounted within the wet chamber 18 adjacent to transducer 2. The positioning encoder 4 provides positional information as to the current position of transducer 2 to the control and data processing system (not shown) connected thereto by connecting wire or conductor 7. Encoder 4 can, for example, comprise a conventional optical encoder which provides positional information based on light reflected from an encoder disk (not shown) extending around the lower periphery of transducer support 2a.

The flexible membrane 10 compensates for any expansion or contraction of the fluid within wet chamber W by flexing in response to such expansion or contraction. In other words, the flexibility of membrane 10 permits the volume of the fluid within the wet chamber W to expand or contract. The passages through the flexible membrane 10 for the flexible circuits 6 and the encoder circuit conductor 7 are sealed by a suitable sealant such as, for example, silicone or polyurethane glue. The flexible membrane 10 is secured in place by a support member 15 which is screwed in place on the proximal end of housing 5. An endoscope tube (not shown) is connected to the tip housing 5 by mounting thereof on the shoulder 15a of support member 15. The housing 5 can be similarly adapted to be mounted at the distal portion of laparoscopic probe. In a specific, non-limiting example, the approximate dimensions of the transducer tip assembly of FIG. 1 are a height or diameter of 12 mm and a length of 35 mm.

Figure 2:
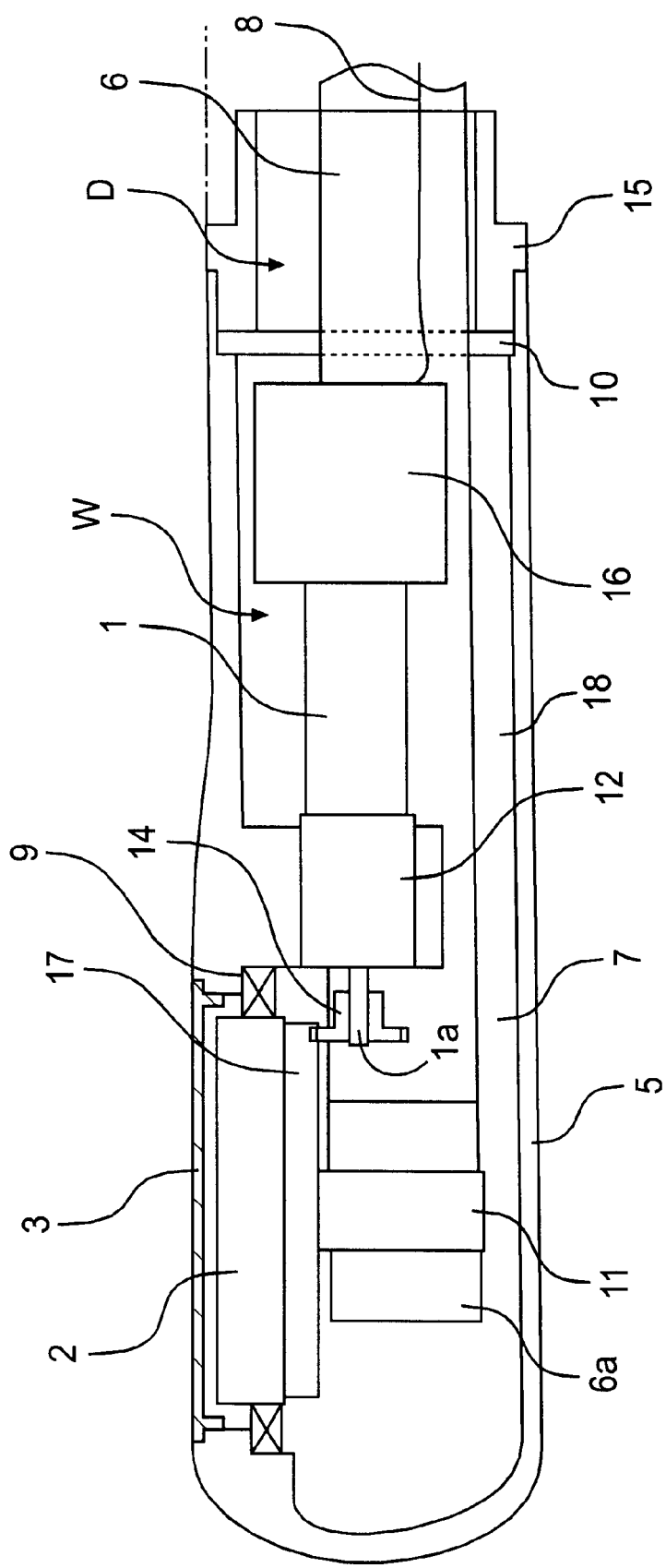
FIG. 2 is a cross sectional view, similar to that of FIG. 1, of a further preferred embodiment of the invention.

Referring to FIG. 2, there is shown a transducer tip in accordance with a further preferred embodiment of the invention. The transducer tip is similar to that of the transducer tip shown in FIG. 1 (and like elements have been given the same reference numerals) except that the position encoder 4 shown in FIG. 1 is replaced by a cylindrical micro-encoder or encoding device 16 mounted directly on the motor 1. In order to make the encoder 16 compatible with liquid immersion, i.e., to permit immersion thereof in the coupling fluid in wet chamber W, the encoder 16 utilizes miniaturized Hall effect sensors (not shown) that detect rotating magnets (not shown). The Hall effect sensors are disposed in a regular or uniform manner around the periphery of the device 16, and therefore the signals obtained thereby are phase shifted accordingly.

Figures 3, 3A:
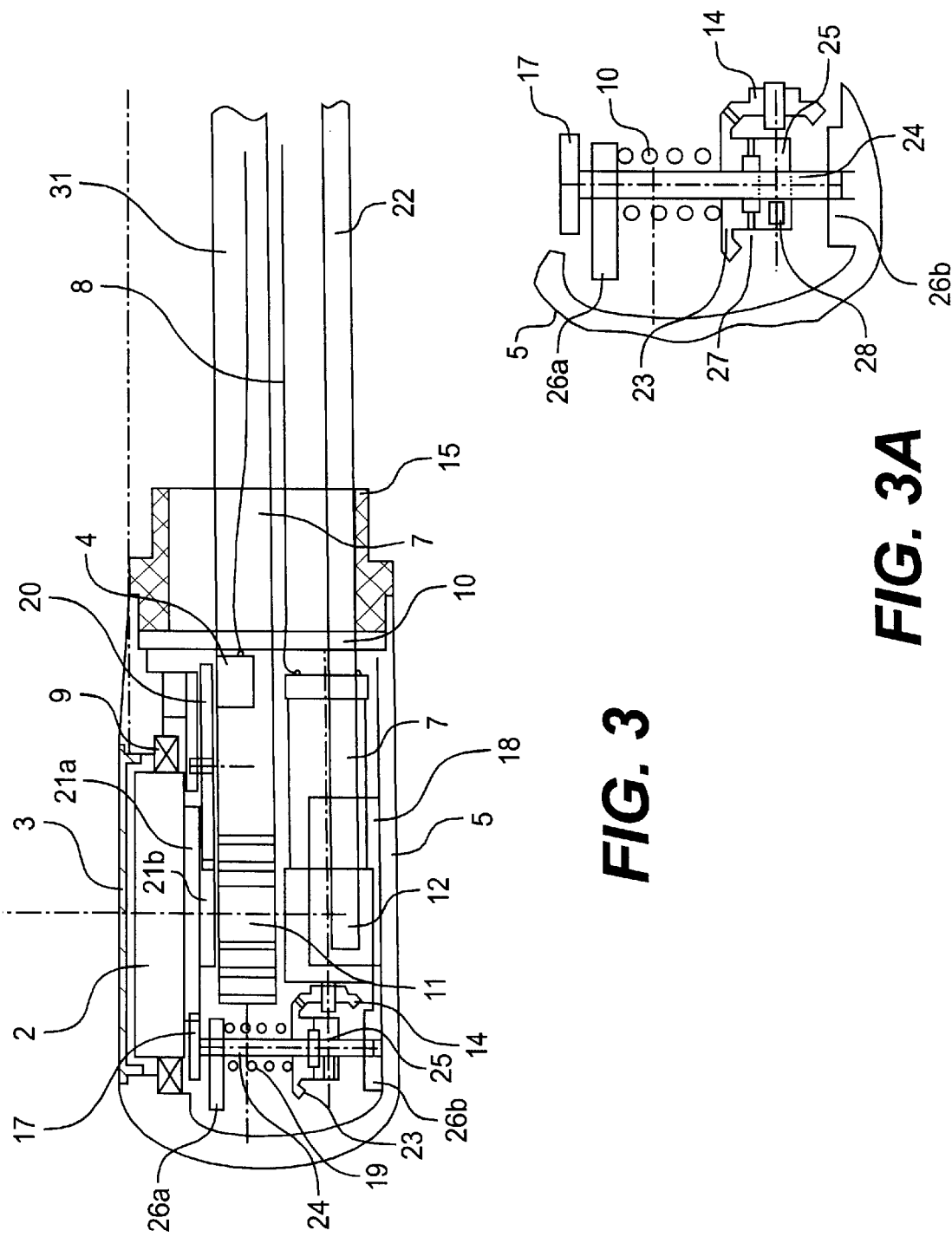
FIG. 3 is a cross section view, similar to that of FIG. 1, of yet another embodiment of the invention.
FIG. 3A is detail of the distal end portion of the device of FIG. 3 showing the gearing arrangement.

Referring to FIG. 3, there is shown a transducer tip in accordance with yet another embodiment of the invention. This embodiment is similar to previous embodiments and, again, like elements are given the same reference numerals. In this embodiment, a motor 1 is placed directly under the rotating transducer 2 to minimize the overall length of the tip. This construction, which can be incorporated into a volume of about 2 cubic centimeters, includes many of the same components as the embodiments of FIG. 1 and comprises in addition to the phased-array transducer 2 and motor 1, an integral gearbox 12, an electrical connector 22, a transmission gearbox or gear assembly, best seen in FIG. 3A, formed by elements 14, 17, 19, 23 and 25 described below, and a position encoder 4, all arranged as shown.

In order to reduce the package size of the components used, high density multilayer flex-print circuits 31 are used to provide the transducer connections instead of the flexible circuits 6 depicted in FIG. 1. The high density multilayer flex-print circuits 31 have a height which is only one half of that of the flexible circuits 6 described in connection with FIG. 1.

In the embodiment of FIG. 3, the transducer 2 is equipped with first and second gears 21a and 21b. Gear 21a, which is of a larger diameter than gear 21b, engages gear 17 driven by motor 1 through gearbox 12. As illustrated, gear 21b is affixed to the underside of gear 21a and engages a further gear 20 that supports an encoding disk (not shown) on the surface thereof that is sensed by a position encoder 4. It is important to understand that the gear reduction ratio between gears 21b and 20 is determined based on the number of rotations that transducer 2 is to undergo. In the specific embodiment under consideration, transducer 2 is capable of rotating through two complete turns. In practice, in order to achieve this, the gear reduction ratio between the gears 21b and 20 should be slightly in excess of two in order to accommodate start and stop portions on the same encoder disk. Gear 20 is also equipped with a mechanical abutment system (not shown) which serves to stop rotation of the transducer 2 in a case where positional information is lost, i.e., when encoder 4 cannot perform this function. In this embodiment, the rotational drive produced by the motor 1 is coupled to the transducer 2 through gearbox 12 and the gears 14, 23, 25 and 17 disposed in the front or forward end of the housing 5. Gear 17 is mounted on a shaft 24 supported within housing 5.

As best seen in FIG. 3A, gear 17 is secured to the shaft 24 at one end thereof and shaft 24 freely rotates within an internal mounting structure formed integrally with housing 5 and including parts 26a and 26b. Gears 23 and 25 are mounted together on the lower end of shaft 24. Gear 25 is secured to shaft 24 by a needle screw or set screw 28 while gear 23 is pressed into mating engagement with gear 25 by a spring 19. In other words, spring 19 exerts a pressure on gear 23 that provides mating engagement between gears 23 and 25. The mating area between gears 23 and 25 can, for example, comprise respective friction surfaces or micro gearing. In addition, the outer diameter of gear 23 engages gear 14 driven by motor 12.

Should the encoder 4 fail to produce an output accurately representative of the actual position of the transducer 2, and the transducer 2 is rotated to the rigid mechanical stop (not shown), gear 23 will be constrained, and thus will compress the spring 19 or otherwise overcome the frictional forces exerted thereon by spring 19, and disengage from gear 25, thereby preventing damage to the transducer 2, gearbox 12 and multilayer flexible circuits 31. This translation of gear 23 and corresponding compression of spring 19 is a product of the fact the gear teeth of gear 23, being of an angular and involuted shape, will exert a tangential force on the mating gear teeth of gear 25 and causes disengagement of the meshing teeth. When the gears 23 and 25 disengage, only gear 23 translates and gear 17 no longer drives transducer 2. It will be understood that gears 14, 17, 23, 21a and 21b can take other forms and shapes (e.g., straight, conical or unshaped) and still provide the transmission requirements discussed above.

Figure 4:
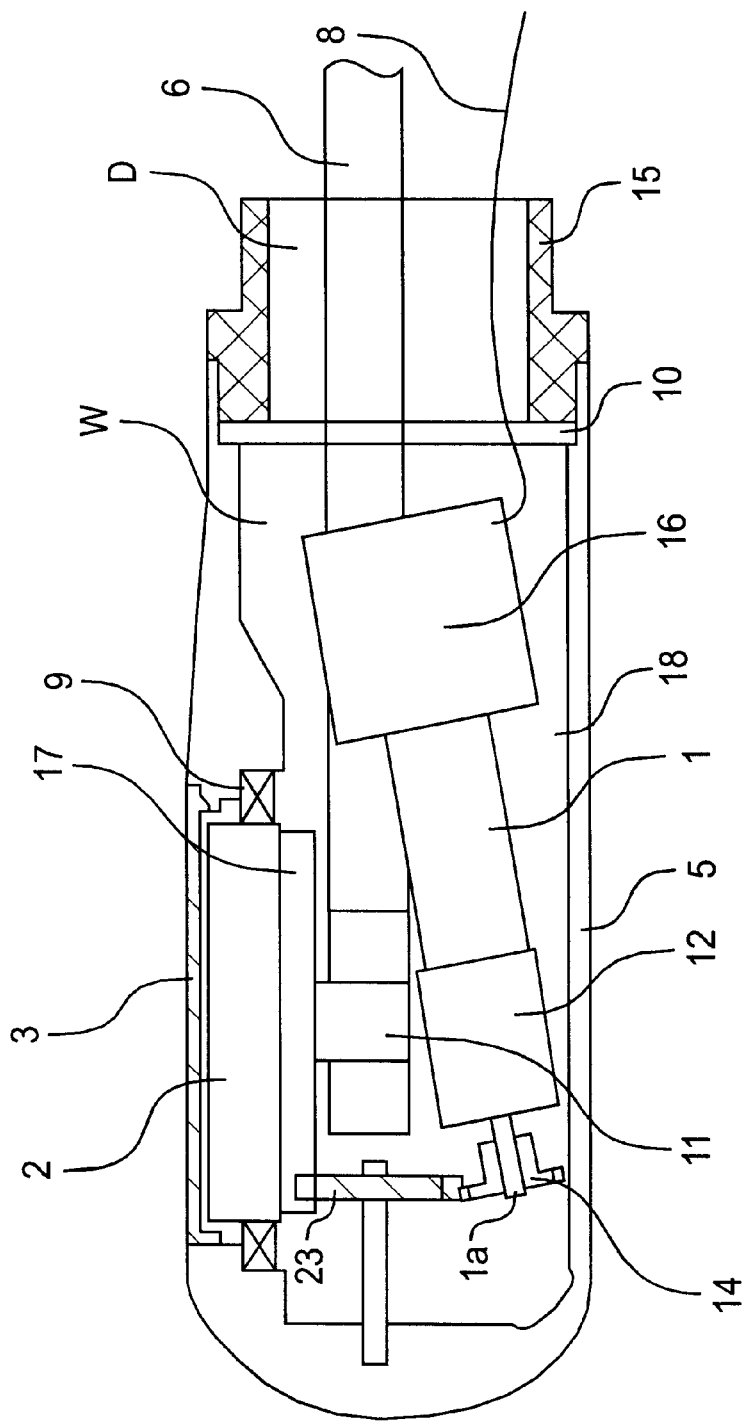
FIG. 4 is a cross sectional view, also similar to that of FIG. 1, of still another embodiment of the invention.

Referring to FIG. 4, yet another preferred embodiment of the transducer tip of the invention is shown. Again, the transducer tip of FIG. 4 includes many of the same elements as the transducer tip depicted in FIG. 1 and like elements have been given the same reference numbers. In this embodiment, the motor 1 is equipped with an encoder 16 as in other embodiments, but because of the larger diameter of the encoder 16, the overall motor assembly, comprising the motor 1, the encoder 16 and the gearbox 12, are mounted obliquely within housing 5. As above, a Hall effect encoder is preferred for use as encoder 16 since the motor 1 is immersed in liquid.

A limited number of motors are suitable for use in the embodiments discussed above, i.e., satisfy the requirements associated with these embodiments, and in particular, the immersion requirement. Brushless, magnetic, and synchronous motors can be used. In a preferred embodiment, the motor comprises a synchronous type motor equipped with a planetary gearbox 12 such as manufactured by RMB, Switzerland. To improve the lifetime of the immersed motor assembly, a dielectric lubricant fluid is preferably used as a coupling medium, and liquids from the family of silicon oils are suitable for this purpose. In a preferred embodiment wherein a synchronous motor is used, the motor 1 includes conventional means for desynchronizing the motor is a predetermined torque output is exceeded.

Although the invention has been described above in relation to preferred embodiments thereof, it will be understood by those skilled in the art that variations and modifications can be effected in these preferred embodiments without departing from the scope and spirit of the invention.

What is claimed is:

1. An ultrasonic phased array imaging transducer device comprising:

a housing having a longitudinal axis, a tip end and a base end;

said housing including a fluid volume containing:

a phased array transducer disposed in the tip end of said housing and oriented so as to provide a sound path extending perpendicular to the longitudinal axis of the housing;

a fluid immersed motor for rotating the transducer;

an encoder for determining positional information with respect to the transducer;

a flexible cable electrically connected to said transducer and coiled elative to said transducer so as to permit transducer rotation of more than 180 degrees;

a torque limitation device for limiting torque transmitted to the transducer, said torque limitation device including intermediate gearing between the transducer and the motor providing a reduction in gear ratio at the transducer and clutch means for disengaging the motor from the transducer responsive to torque in excess of a predetermined value so as to prevent damage to said flexible cable and;

a static flexible membrane for sealing the fluid volume, said flexible cable extending through the flexible sealing membrane.

2. An ultrasonic phased array transducer device according to claim 1, wherein the membrane comprises an elastic member which expands so as to compensate for expansion of the fluid in the wet chamber.

3. An ultrasonic phased array transducer device according to claim 1, wherein said motor includes a drive shaft and said intermediate gearing of the torque limitation device comprises a first gear fixed to the drive shaft of the motor, a second gear directly mounted on the transducer, and a third gear linking the first gear and the second gear so as to provide transmission of rotary drive from the first gear to the second gear.

4. An ultrasonic phased array transducer device according to claim 3, wherein said clutch means includes gear mounting means for mounting said third gear so as to provide disengagement of said transmission responsive to torque in excess of a predetermined value being exerted on said transducer.

5. An ultrasonic phased array transducer device according to claim 4, wherein said intermediate gearing of said torque limitation device includes a fourth gear engaging said second gear and mounted on :a support shaft, and said clutch means includes a further gear affixed to said support shaft and said gear mounting means includes a spring for biassing said third gear into engagement with said further gear such that, when said third gear and said further gear are engaged, said third gear provides said transmission and, when said third gear and said further gear are disengaged, said transmission is interrupted.

6. An ultrasonic phased array transducer device according to claim 1, wherein the transducer includes a peripheral gear and said encoder includes an encoder gear engaged with said peripheral gear of said transducer and a mechanical abutment arrangement for providing mechanical limiting of the rotation of the transducer.

7. An ultraphonic phased array transducer device according to claim 6, wherein the encoder comprises a single encoder disk and the peripheral gear and the encoder gear provide a gear reduction ratio permitting rotation of the transducer more than 360° with said single encoder disk.

8. An ultrasonic phased array transducer device according to claim 1, wherein the motor comprises a synchronous motor including means for desynchronizing the motor if a predetermined torque output is exceeded.

9. An ultrasonic phased array transducer device according to claim 1 wherein said tip and base of said housing have an anatomical shape adapted to fit onto a fingertip of a user.

10. An ultrasonic phased array transducer device according to claim 1, wherein the housing is adapted to be mounted to an endocavity ultrasound probe.

11. An ultrasonic phased array transducer device according to claim 1, wherein the housing is adapted to be mounted at a distal portion of a laparoscopic probe.

12. An ultrasonic phased array imaging transducer device comprising:

a housing having a longitudinal axis, a tip end and a base end;

said housing including a fluid volume containing:

a phased array transducer disposed in the tip end of said housing and oriented so as to provide a sound path extending perpendicular to the longitudinal axis of the housing, said transducer including a peripheral gear;

a fluid immersed motor for rotating the transducer;

an encoder for determining positional information with respect to the transducer, said encoder including an encoder gear engaged with said peripheral gear of said transducer and a mechanical abutment arrangement for providing mechanical limiting of the rotation of the transducer;

a flexible cable electrically connected to said transducer and coiled relative to said transducer so as to permit transducer rotation of more than 180 degrees;

a torque limitation device for limiting torque transmitted to the transducer; and a static flexible membrane for sealing the fluid volume, said flexible cable extending through the flexible sealing membrane.

13. An ultraphonic phased array transducer device according to claim 12, wherein the encoder comprises a single encoder disk and the peripheral gear and the encoder gear provide a gear reduction ratio permitting rotation of the transducer more than 360° with said single encoder disk.

14. An ultrasonic phased array imaging transducer device comprising:

a housing having a longitudinal axis, a tip end and a base end;

said housing including a fluid volume containing:

a phased array transducer disposed in the tip end of said housing and oriented so as to provide a sound path extending perpendicular to the longitudinal axis of the housing;

a fluid immersed motor for rotating the transducer;

an encoder for determining positional information with respect to the transducer, said encoder comprising a single encoder disk coupled to said transducer so as to permit transducer rotation of more than 360°;

a flexible cable electrically connected to said transducer and coiled relative to said transducer so as to permit transducer rotation of more than 360°;

a torque limitation device for limiting torque transmitted to the transducer; and a static flexible membrane for sealing the fluid volume, said flexible cable extending through the flexible sealing membrane.

* * * * *

UNITED STATES PATENT AND TRADEMARK OFFICE
CERTIFICATE OF CORRECTION

PATENT NO.   : 6,425,870 B1
DATED        : July 30, 2002
INVENTOR(S)  : Flesch

It is certified that error appears in the above-identified patent and that said Letters Patent is hereby corrected as shown below:

<u>Column 7,</u>
Line 36, change "ultraphonic" to -- ultrasonic --.

<u>Column 8,</u>
Line 24, change "ultraphonic" to -- ultrasonic --.

Signed and Sealed this

Third Day of December, 2002

JAMES E. ROGAN
*Director of the United States Patent and Trademark Office*